United States Patent [19]

Escher et al.

[11] Patent Number: 6,129,941

[45] Date of Patent: Oct. 10, 2000

[54] 1-METHOXY-3-HEXANETHIOL AND ITS S-ACETYL DERIVATIVE AS PERFUMING AND FLAVORING INGREDIENTS

[75] Inventors: Sina Dorothea Escher, Confignon; Matthijs Van De Waal, Laconnex, both of Switzerland

[73] Assignee: Firmenich SA, Geneva, Switzerland

[21] Appl. No.: 09/373,906

[22] Filed: Aug. 13, 1999

[30] Foreign Application Priority Data

Aug. 21, 1998 [CH] Switzerland .................. 1718/98

[51] Int. Cl.⁷ .................. A23L 1/226; C11D 3/34; A61K 7/46; C07D 331/02; C07D 303/23
[52] U.S. Cl. .................. 426/535; 424/65; 424/76.1; 426/650; 510/101; 510/107; 512/7; 549/90; 549/554; 558/252; 568/62
[58] Field of Search .................. 558/252; 568/62; 510/101, 107; 512/7; 426/535; 549/90, 554

[56] References Cited

U.S. PATENT DOCUMENTS 3,970,689   7/1976   Stoffelsma et al. .................. 426/535 X

OTHER PUBLICATIONS

T.E. Furia & N. Bellanca, "Fenaroli's Handbook of Flavor Ingredients, 2nd Edition", 1992, CRC Press, Boca Raton pp. 327–328 "CLARY".

K–H Engel et al., "Identification of New Sulfur–Containing Volatiles in Yellow Passion Fruits (*Passiflora edulis* f. flavicarpa)", *J. Agric. Food Chem.*, vol. 39, No. 12, pp. 2249–2252 (1991).

*Primary Examiner*—Michael G. Ambrose
*Attorney, Agent, or Firm*—Pennie & Edmonds LLP

[57] ABSTRACT

A compound of formula

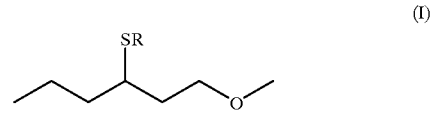

(I)

wherein R represents a hydrogen atom or an acetyl group, is useful in perfumery and in the field of flavors. The compound of formula (I) confer an odor and flavor effect extremely powerful of the clary-sage type, even when used in small amounts.

16 Claims, No Drawings

1-METHOXY-3-HEXANETHIOL AND ITS S-ACETYL DERIVATIVE AS PERFUMING AND FLAVORING INGREDIENTS

BRIEF SUMMARY OF THE INVENTION

The present invention relates to the perfume and flavor industries. It concerns more particularly a compound of formula

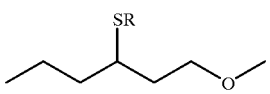
(I)

wherein R represents a hydrogen atom or an acetyl group, and its use as perfuming or flavoring ingredient.

Another object of the invention is a process for the preparation of a compound of formula (I).

BACKGROUND OF THE INVENTION

To our knowledge, there is no mention nor description in the chemical literature of any synthesis of the ethers of formula (I), neither any description of their taste or odor.

DETAILED DESCRIPTION OF THE INVENTION

Surprisingly, we have now been able to establish that the compounds of formula (I) possess some odor and organoleptic properties, which render them very useful for the perfume and flavor industries. More particularly, the compounds (I) present a very natural and particularly powerful odor and taste thus providing typical and well-marked organoleptic effects, when said compounds are incorporated in a perfume or a flavor, even at high dilutions.

The compound of formula (I) wherein R represents an acetyl group, i.e. S-[1-(2-methoxyethylbutyl]ethanethioate, presents an odor with a typical sulfury note, accompanied by box-tree (Buxus), blackcurrant and onion type notes, which odor is reminiscent of the odor of sage.

The compound of formula (I) wherein R represents a hydrogen atom, i.e. 1-methoxy-3-hexanethiol, is particularly appreciated by the perfumers and flavorists and is therefore a preferred ingredient of the invention. This compound also develops an odor of the sulfur type. Moreover, its fragrance presents very natural green and herbaceous odor notes, and can be described as being reminiscent of the odor of the clary-sage. Now, the inventors of the present application have been able to discover that 1-methoxy-3-hexanethiol is a component of natural clary-sage and is moreover a key substance of the clary-sage characteristic odor, indispensable for an artificial reconstitution of this fragrance. Furthermore, this compound turns out to provide the really sought after note which makes the difference between the typical odor of a field of clary-sage in flower, and the typical odor of the commercial essential oil of this plant.

In fact, the clary-sage flowers diffuse an odor wherein a slight sulfury-green note can be perceived. This odor is reminiscent of the odor of human armpit and is thus a bit offensive, however it is welcome and appreciated owing to the equilibrium between this note and the other odor notes characteristic of this flower, which thus form the typical odor of clary-sage. On the other hand, the commercially available essential oil is totally devoid of this sulfury note.

The natural occurrence of 1-methoxy-3-hexanethiol was revealed thanks to a very complex method, resorting to a combination of fractionation techniques with liquid and gas chromatography and mass spectrometry.

The compound of formula (I) wherein R represents a hydrogen atom was isolated from its natural state i.e. from clary-sage, by the method represented in the scheme 1 hereafter:

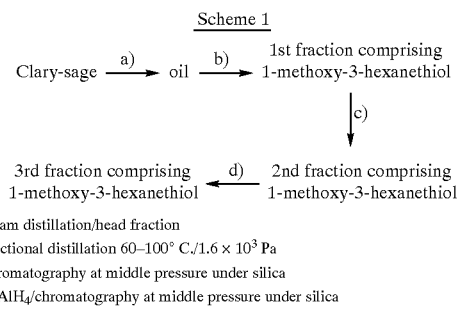

a) steam distillation/head fraction
b) fractional distillation 60–100° C./1.6 × 10³ Pa
c) chromatography at middle pressure under silica
d) LiAlH₄/chromatography at middle pressure under silica As represented in scheme 1, a steam distillation of freshly cut clary-sage plant was carried out and the head fraction was collected to provide 16 g of an oil diffusing the desired sulfury odor. Said oil was fractionated under low pressure on a Fisher type column covered with Teflon®. The fraction obtained at the temperature and pressure indicated here above was subjected to a chromatography at middle pressure on a Lobar B type column, using a pentane/diethyl ether mixture as eluting agent. As it happened, the obtained fraction still comprised some products which prevented identification by mass spectrometry of the desired compound, thus requiring a LiAlH$_4$ treatment followed by hydrolysis and again a chromatography step, as described above. Therefore, a still complex mixture was obtained, containing a few products and the desired 1-methoxy-3-hexanethiol, which could then be identified by gas chromatography/mass spectrometry coupling analysis.

1-Methoxy-3-hexanethiol presented the following characteristics:

Retention index: 1365 (Supelcowax 10 type polar column, 60 m long, 0.25 mm i.d.; T=80–240° C., isotherm. 5 min, 5° C./min)

Mass spectrum: 148(4), 116(14), 114(4), 88(14), 83(14), 82(7), 71(36), 67(10), 58(9), 55(38), 47(13), 45(100), 41(35); a peak was obtained at m/z=166[M+NH$_4$]$^+$ by chemical ionization in the presence of NH$_3$.

Alternatively, step d) in the above scheme was replaced by an adsorption of the previously obtained fraction, under an agarose organomercurial gel which specifically retains products such as mercaptan. An elution of the agarose with an excess of 1,4-dithiothreitol in a 10M dichloromethane solution provided the final fraction containing 1-methoxy-3-hexanethiol.

The compound's structure was deduced from the mass spectrum and confirmed by synthesis.

The preparation of the ethers (I) is another object of the invention. The synthesis is carried out in three (when R is a hydrogen atom), respectively four (when R is an acetyl group) steps, according to the following scheme:

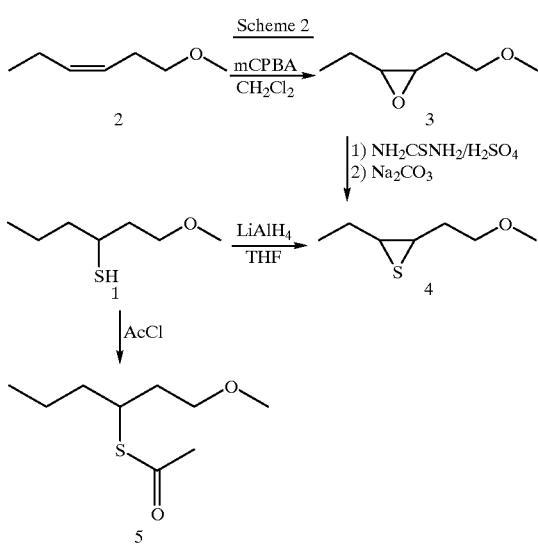

Scheme 2 mCPBA = m-chloroperbenzoic acid

The process for the preparation of the compounds of the invention is characterized in that it comprises the reduction of cis-2-ethyl-3-(2-methoxyethyl) thiirane (4) to 1-methoxy-3-hexanethiol (1). 2-Ethyl-3-(2-methoxyethyl)thiirane (4) is prepared from 2-ethyl-3-(2-methoxyethyl)oxirane (3) in the presence of thiourea. The intermediates (3) and (4) in the synthesis represented in scheme 2 are novel.

The odor and flavor properties of the flavor compounds of the invention appear as totally unexpected in view of the prior art which is totally silent with regard to these compounds.

Furthermore, although the ethers according to the invention and namely 1-methoxy-3-hexanethiol lend themselves particularly well to the reconstitution of the odor of clary-sage, in particular when used in diluted concentrations, these compounds are also surprisingly useful in other types of perfumes or perfuming compositions wherein a sulfury-herbaceous and green note is sought. One can mention for instance perfumes or perfuming compositions of the herbaceous-aromatic type, which acquire a well appreciated natural connotation and diffusion reminiscent of clary-sage when 1-methoxy-3-hexanethiol in particular is added thereto. In a general manner, the compounds of the invention are very advantageous for perfuming compositions or perfumes when used as boosters, i.e. as compounds susceptible of reinforcing and improving the global impression of a given composition, thus outlining and rounding the odor properties of this composition.

We have thus been able to establish that namely 1-methoxy-3-hexanethiol, when in a pure state and separated from other substances which are present in clary-sage, can be used in a wide range of concentrations to create fragrance and taste effects totally unsuspected heretofore and as mentioned above in many cases quite distinct from those obtained with natural clary-sage oil.

The ethers of the invention can suit almost all the fields of modern perfumery. One can cite the applications in fine perfumery, namely in the creation of perfumes and colognes wherein novel and original odor effects can be obtained.

The compounds (I) can also be used in functional perfumery, namely to perfume soaps, shower or bath gels, shampoos, body deodorants and antiperspirants, ambient air deodorants, liquid or solid detergents for textile treatment, detergent compositions or cleaning products for dishes or varied surfaces, or cosmetic preparations.

In these applications, the compounds according to the invention can be used alone, as well as mixed with other perfuming ingredients, solvents or additives commonly used in perfumery. The nature and variety of these coingredients do not require a more detailed description here, which would not be exhaustive anyway. In fact, a person skilled in the art, having a general knowledge, is able to choose them according to the nature of the product that has to be perfumed and the olfactory effect sought. These perfuming coingredients belong to varied chemical groups such as alcohols, aldehydes, ketones, esters, ethers, acetates, nitrites, terpernic hydrocarbons, heterocyclic nitrogen- or sulfur-containing compounds, as well as natural or synthetic essential oils. Many of these ingredients are listed in reference texts such as S. Arctander, Perfume and Flavor Chemicals, 1969, Montclair, N.J., USA, or more recent versions thereof, or in other similar books.

The proportions in which the compounds according to the invention can be incorporated in the different products mentioned above vary in a broad range of values. These values depend on the nature of the product that has to be perfumed and on the olfactory effect sought, as well as on the nature of the coingredients in a given composition when the compounds of the invention are used in admixture with perfuming coingredients, solvents or additives commonly used in the art.

In a general manner, the compounds according to the invention will be used in small amounts, typically at very high dilutions, owing to their strong odor impact.

For instance, concentrations from 1 ppm to 1%, and preferably from 10 ppm to 0.1% by weight of these compounds, with respect to the weight of the perfuming composition in which they are incorporated, can typically be used. Much lower concentrations than these can be used when these compounds are directly applied for perfuming some of the consumer products mentioned above.

The compounds of the invention are also useful in the field of flavors, i.e. to impart taste and texture to flavoring compositions and foods or beverages for example.

Their taste is typically associated with the characteristic taste of exotic fruits, in combination with a mint note of the garden mint type. In particular, the taste of 1-methoxy-3-hexanethiol is also reminiscent of grapefruit, and its global organoleptic impression can thus be described as being fruity-green and exotic.

Thanks to the above mentioned characteristics, the compounds of the invention are particularly suitable for the flavoring of products which require a fruity taste such as fruit-based foods and beverages, desserts, compotes and fruit jams, yoghurts and other dairy products, ice creams, chewing-gums or pharmaceutical preparations.

The ethers (I) can also be used in savory flavors, in particular in flavors of the meat type, in order to reinforce the typical meat taste and to round the global impression. Non-limiting examples of this type of applications include soups and stocks, stock cubes, dressings, snacks, sauces or ready cooked dishes.

In these applications, the compounds according to the invention will typically be used in concentrations of the order of 0.005 to 5.0 ppm, preferably from 0.01 to 2.0 ppm, with respect to the foods into which they are incorporated. Much higher concentrations can be chosen when the compounds are used in concentrated flavors or flavoring compositions which will be incorporated in consumer products.

The compounds (I) of the invention thus make it possible to confer, improve, enhance or modify the odor or taste of consumer products, as well as of perfuming bases or concentrates, or yet flavor preparations and compositions. In other words, they can impart to the latter their characteristic odor or taste, as the case may be, thus modifying and/or improving the original odor and taste properties of the products and compositions in which they are incorporated. These products thus become more appealing to the consumer and have an enhanced odor or taste impact, or both.

The invention will be now described in greater detail in the following examples, wherein the abbreviations have the usual meaning in the art, the temperatures are indicated in degrees centigrade (° C.); the NMR spectral data (chemical displacement $\delta$) are indicated in ppm with respect to the TMS as standard.

EXAMPLE 1

Synthesis of 1-methoxy-3-hexanethiol a) cis-2-Ethyl-3-(2-methoxyethyl)oxirane (3)

27.4 g of (Z)-1-methoxy-3-hexene were dissolved in dichloromethane (850 ml) and cooled to 10°. 62 g of ca 70% m-chloroperbenzoic acid corresponding to 1.05 eq., were added in portions. The mixture was allowed to react during 15 hours and was then transferred into an extraction funnel wherein it was washed with an aqueous solution of NaOH and then with water to neutrality. After separation and drying of the organic layer on $Na_2SO_4$, the residue was distilled over a 5 cm long Vigreux type column at $51–52°/1.5 \times 10^3$ Pa to give 24.9 g (80%) of the desired compound in the form of a colourless liquid which presented the following analytical data:

$^1$H-NMR: 1.13(t, J=6.2, 3 H—C(6)); 1.55(ABX$_2$Z, 2 H—C(5)); 1.79(ABX$_2$Z, 2 H—C(2)); 2.90(m, H—C(4)); 3.05(m, H—C(3)); 3.37(s, H$_3$CO); 3.54(dxd, J$_1$=5.0, J$_2$=5.0, 2 H—C(1)). $^{13}$C-NMR; 10.49(q, C(6)); 21.23(t, C(5)); 28.39 (t, C(2)); 54.82(d, C(3)); 58.15(d, C(4)); 58.81(q, CH$_3$O); 70.09(t, C(1)). MS: 129(1, M$^+$−1), 115(1), 99(4), 85(26), 72(16), 67(12), 59(26), 45(100), 41(68).

b) cis-2-Ethyl-3-(2-methoxyethyl)thiirane (4)

24.9 g of the epoxide obtained under a) were added dropwise to a solution of 14.5 g of thiourea in a cooled water/conc. $H_2SO_4$ (ca 12:1) mixture. After addition, the solution was stirred at room temperature during 15 hours. The reaction medium was then poured in frozen water and the pH was adjusted to 10 by means of $Na_2CO_3$. The mixture was then heated to 40° during 40 minutes, the reaction was completed. The obtained solution was extracted by means of ether, washed to neutrality, dried and concentrated. A distillation of the raw product at $69–73°/1.5 \times 10^3$ Pa provided 25 g (90%) of the pure desired product, presenting the following analytical data:

$^1$H-NMR: 1.05(t, J=6.2, 3 H—C(6)); 1.52(m, 1 H—C(5)); 1.67(m, 1 H—C(2)); 1.88(m, 1 H—C(5)); 2.20(m, 1 H—C(2)); 2.95(m, H—C(4)); 3.09(m, H—C(3)); 3.38(s, H$_3$CO); 3.57(m, 2 H—C(1)). $^{13}$C-NMR; 13.79(q, C(6)); 24.45(t, C(5)); 31.06(t, C(2)); 38.94(d, C(3)); 43.36(d, C(4)); 58.81 (q, CH$_3$O); 72.32(t, C(1)). MS: 148(0,5, M$^+$+2), 147(0,5, M$^+$+1), 146(7, M$^+$), 113(28), 101(2), 99(2), 81(20), 71(38), 67(13), 59(18), 45(100).

c) 1-Methoxy-3-hexanethiol (1)

A solution of 15 g of thioepoxide obtained under b) in 50 ml of THF was added dropwise to a suspension of 1.9 g of LiAlH$_4$ in 200 ml of abs. THF. The solution was heated to reflux for 4 hours and then was allowed to react at room temperature for 15 hours. The reaction medium was poured in frozen water, extracted by means of ether, the organic layer was separated and washed with 10% HCl aq., water and NaHCO$_3$. After drying over Na$_2$SO$_4$ and distillation of the solvent, the separation of the obtained raw product was carried out on a Lobar C type column by means of a hexane/diethyl ether mixture as elution agent. The separation was followed by gas chromatography. The fraction of the desired product was purified by distillation on a bulb to bulb oven at $70°/1.5 \times 10^3$ Pa to yield 3.3 g (22%) of pure product presenting the following analytical data:

$^1$H-NMR: 0.93(t, J=6.2, 3 H—C(6)); 1.38(d, HS); 1.6–1.4 (m, 2 H—C(4), 2 H—C(5)); 1.65(m, 1 H—C(2)); 1.97(m, 1 H—C(2)); 2.94(m, H—C(3)); 3.34(s, H$_3$CO); 3.53(m, 2 H—C(1)). $^{13}$C-NMR; 13.76(q, C(6)); 20.18(t, C(4 or 5)); 37.58(d, C(3)); 38.82(t, C(2)); 41.47(t, C(4 or 5)); 58.68(q, CH$_3$O); 70.30(t, C(1)). MS: 150(0.5, M$^+$+2). 149(0.5, M$^+$+1), 148(6, M$^+$), 116(22), 114(10), 101(4), 88(26), 71(61), 67(14), 55(39), 47(12), 45(100), 41(34).

EXAMPLE 2

Synthesis of S-[1-(2-methoxyethyl)butyl] ethanethioate

The compound was synthesized in one step from 1-methoxy-3-hexanethiol prepared as described in example 1.

To an ice-cooled and stirred solution of 296 mg of 1-methoxy-3-hexanethiol (2 mmol) in 2 ml of anhydrous pyridine, were added dropwise via syringe 280 $\mu$l of acetyl chloride (4 mmol). The mixture was allowed to warm to room temperature and was stirred overnight. It was then diluted with water (10 ml). The organic matter was extracted with diethyl ether (2×40 ml). The ether layer was washed with 2 N H$_2$SO$_4$ (3×10 ml), saturated NaHCO$_3$ (1×10 ml) followed by saturated NaCl (1×10 ml). After drying over anhydrous Na$_2$SO$_4$, the solvent was evaporated under reduced pressure and the residue was distilled at $130–140°/15 \times 10^2$ Pa to give 320 mg (84.2%) of (S)-[1-(2-methoxyethyl)butyl]ethanethioate as a colorless liquid presenting the following analytical data:

$^1$H-NMR: 0.91(t, J=6.2, 3 H—C(4)); 1.38(m, 2 H—C(3)); 1.58(m, 2 H—C(2)); 1.80 and 1.90(2m, 2 H—C(1')); 2.32(s, H$_3$CCO); 3.32(s, H$_3$CO); 3.42(m, 2 H—C(2')); 3.62(m, H—C(1)). $^{13}$C-NMR: 13.87(q, C(4)); 20.00(t, C(3)); 30.75 (q, CH$_3$CO); 34.72(t, C(1')); 37.30(t, C(2)); 41.49(d, C(1)); 58.65(q, CH$_3$O); 70.24(t, C(2')); 198.71(s, CH$^3$CO). MS: 192(0.2, M$^+$+2), 191(0.2, M$^+$+1), 190(3, M$^+$), 147(41, M$^+$−$^{CH}$$_3$CO, S isotope satellites present), 115(19), 88(24), 71(47), 55(43), 47(8), 45(100), 43(98).

EXAMPLE 3

Preparation of a perfume of the aromatic-citrus, woody lavender type

A perfume for men was prepared by admixing the following ingredients:

| Ingredients | Parts by weight |
| --- | --- |
| Absinthe essential oil | 10 |
| Allyl amyl glycolate | 10 |
| Aspic essential oil | 100 |
| Bergamot essential oil | 100 |
| 10% * Cetalox ®[1)] | 15 |
| Sfuma lemon essential oil | 50 |
| 4-Cyclohexyl-2-methyl-2-butanol | 70 |
| Coumarine | 10 |
| 1% * α-Damascone | 10 |

| Ingredients | Parts by weight |
| --- | --- |
| Dihydromyrcenol | 100 |
| 10% * Estragole | 25 |
| 10% * Eugenol | 25 |
| Mayol ®[2] | 20 |
| 10% * Rose oxide | 10 |
| Patchouli oil | 70 |
| 10% * Polysantol ®[3] | 40 |
| Benzyl salicylate | 250 |
| 10% * White thyme oil | 5 |
| 10% * Zestover[4] | 30 |
| Total | 950 |

* in dipropylene glycol
[1] 8,12-epoxy-13,14,15,16-tetranorlabdane; origin: Firmenich SA, Geneva, Switzerland
[2] cis-7-p-menthanol; origin: Firmenich SA, Geneva, Switzerland
[3] (E)-3,3-dimethyl-5-(2',2',3'-trimethyl-3'-cyclopenten-1'-yl)-4-penten-2-ol; origin: Firmenich SA, Geneva, Switzerland
[4] 2,4-dimethyl-3-cyclohexen-1-carbaldehyde; origin: Firmenich SA, Geneva, Switzerland When 0.005, respectively 0.02, parts per weight of 1-methoxy-3-hexanethiol were added to the above described composition and the mixture was completed with dipropylene glycol to obtain a total of 1000 parts per weight, two novel compositions were obtained. It was observed that the compound of the invention married itself harmoniously to the base composition. It provided, even at a low concentration of 0.005%, a very perceptible natural odor effect of the clary-sage type.

EXAMPLE 4

Reconstitution of clary-sage

An artificial composition with a clary-sage type odor, inspired by the main constituents of clary-sage, was prepared by admixing the following ingredients:

| Ingredients | Parts by weight |
| --- | --- |
| Geranyl acetate | 70 |
| Linalyl acetate | 6500 |
| Neryl acetate | 30 |
| 10% * cis-3-Hexenol acetate | 5 |
| 10% * C9 aldehyde | 1 |
| Camphor | 20 |
| (+)-Carvone | 2 |
| 10% * Cetalox ®[1] | 10 |
| Citronellol | 10 |
| 10% * Coumarine | 2 |
| 1% * Damascenone | 20 |
| Dipropylene glycol | 30 |
| Eucalyptol | 30 |
| Eugenol | 5 |
| Geraniol | 40 |
| Citronella | 20 |
| Linalool | 1500 |
| 10% * Menthone | 10 |
| Myroxyde ®[2] | 50 |
| Nerol | 20 |
| 10% * Nerol oxide | 20 |
| 10% * Pipol | 15 |

| Ingredients | Parts by weight |
| --- | --- |
| Terpineol | 80 |
| 10% * Benzyl tiglate | 10 |
| Total | 8500 |

* in dipropylene glycol
1) see example 3
2) 6,7-epoxy-3,7-dimethyl-octadiene; origin: Firmenich SA, Geneva, Switzerland To this base composition there were added 0.02, respectively 0.06 parts per weight of 1-methoxy-3-hexanethiol and the mixture was completed with dipropylene glycol to obtain a total of 10.000 parts per weight. Two novel compositions were thus obtained. The addition of the compound according to the invention imparted to the base composition a very typical "clary-sage" odor and made it possible to reach the characteristic harmony of the natural clary-sage essential oil. This odor effect was all the more marked in the composition which contained 0.06% of the compound of the invention.

What we claim is:

1. A compound of formula $$\text{(I)}$$

wherein R represents a hydrogen atom or an acetyl group.

2. As a compound of formula (I) according to claim 1, 1-methoxy-3-hexanethiol.

3. A perfuming composition or a perfumed product containing as active ingredient a compound according to claim 1.

4. A perfuming composition or a perfumed product containing as active ingredient 1-methoxy-3-hexanethiol.

5. Perfumed product according to claim 3, in the form of a perfume or a cologne, a soap, a shower or bath gel, a shampoo or another hair-care product, a cosmetic preparation, a body or ambient air deodorant, a detergent or a fabric softener, or a household product.

6. Perfuming composition or perfumed product according to claim 3, characterized in that the concentration of said active ingredient is comprised between 1 ppm and 1% of the total weight of the composition or product.

7. Flavoring composition or flavored product containing as active ingredient a compound according to claim 1.

8. Flavored product according to claim 7, in the form of a fruit based food or beverage, a dessert, a compote or fruit jam, a yogurt, an ice cream or other dairy product, a chewing gum, a pharmaceutical product, a soup or stock, a cube stock, a dressing, a snack, a sauce or a ready cooked dish.

9. Flavoring composition or flavored product according to claim 7, characterized in that the concentration of the active ingredient is comprised between 0.005 and 5.0 ppm of the total weight of the composition or product.

10. A method to confer, improve, enhance or modify the odor or flavor properties of a perfuming composition, a perfumed product, a flavoring composition or a flavored product, which method comprises adding a compound according to claim 1 as perfuming or flavoring ingredient to said composition or product.

11. A method to confer, improve, enhance or modify the odor or flavor properties of a perfuming composition, a perfumed product, a flavoring composition or a flavored product, which method comprises adding 1-methoxy-3-hexanethiol as perfuming or flavoring ingredient to said composition or product.

12. Method to confer, improve or modify the taste character of the fruity or meat type of a flavoring composition or a flavored product, characterized in that a compound according to claim 1 is added to said composition or product.

13. Process for the preparation of a compound according to claim 1, characterized in that said process comprises the reduction of cis-2-ethyl-3-(2-methoxyethyl)thiirane to 1-methoxy-3-hexanethiol.

14. Process according to claim 13, characterized in that cis-2-ethyl-3-(2-methoxyethyl) thiirane is prepared from cis-2-ethyl-3-(2-methoxyethyl)oxirane by reaction with thiourea.

15. cis-2-Ethyl-3-(2-methoxyethyl)thiirane.

16. cis-2-Ethyl-3-(2-methoxyethyl)oxirane.

* * * * *